United States Patent
Collin et al.

(10) Patent No.: US 6,561,011 B2
(45) Date of Patent: May 13, 2003

(54) APPARATUS AND METHOD FOR MEASURING THE VISCOSITY OF PLASTIC MATERIALS

(75) Inventors: Heiner Collin, Munich (DE); Heinrich H. Collin, Vaterstetten (DE)

(73) Assignee: Dr. Collin GmbH, Ebersberg (DE)

( * ) Notice: Subject to any disclaimer, the term of this patent is extended or adjusted under 35 U.S.C. 154(b) by 1 day.

(21) Appl. No.: 09/820,774

(22) Filed: Mar. 30, 2001

(65) Prior Publication Data

US 2001/0013248 A1 Aug. 16, 2001

Related U.S. Application Data

(63) Continuation-in-part of application No. PCT/EP99/07477, filed on Oct. 6, 1999.

(30) Foreign Application Priority Data

Oct. 9, 1998 (DE) .............................. 19846579

(51) Int. Cl.⁷ ............................................. G01N 11/08
(52) U.S. Cl. .................... 73/54.09; 73/54.04; 73/54.05; 73/54.06
(58) Field of Search .................. 73/54.04, 54.05, 73/54.06, 54.09

(56) References Cited

U.S. PATENT DOCUMENTS

| | | | | | |
|---|---|---|---|---|---|
| 3,610,026 A | * | 10/1971 | Topham | .................... | 73/54.09 |
| 4,425,790 A | * | 1/1984 | Bice et al. | .................. | 73/54.09 |
| 4,539,837 A | * | 9/1985 | Barnaby | .................... | 73/54.06 |
| 4,677,844 A | * | 7/1987 | Sonoda | ...................... | 73/54.09 |

FOREIGN PATENT DOCUMENTS

| | | | | | |
|---|---|---|---|---|---|
| DE | 294091 | * | 1/1991 | ................ | 73/54.09 |
| DE | 4220157 | * | 1/1993 | ................ | 73/54.09 |
| DE | 4442172 | * | 5/1996 | ................ | 73/54.04 |
| EP | 595276 | * | 5/1974 | ................ | 73/54.09 |
| GB | 2271856 | * | 4/1994 | ................ | 73/54.04 |
| JP | 2-55933 | * | 2/1990 | ................ | 73/54.09 |
| SU | 587366 | * | 1/1978 | ................ | 73/54.09 |
| SU | 1569672 | * | 6/1990 | ................ | 73/54.04 |

\* cited by examiner

Primary Examiner—Daniel S. Larkin
(74) Attorney, Agent, or Firm—Klaus J. Bach

(57) ABSTRACT

In an apparatus for measuring the viscosity of plastic materials including a heatable housing structure, enclosing a controllable material pump for generating a certain material flow, a plurality of capillaries, a melt distributor is provided in the supply line of the material from the material pump to the capillaries with which the material can be directed to either of the plurality of capillaries and each capillary is provided with a pressure and a material temperature sensor providing the values needed for determining the viscosity of the material.

10 Claims, 5 Drawing Sheets

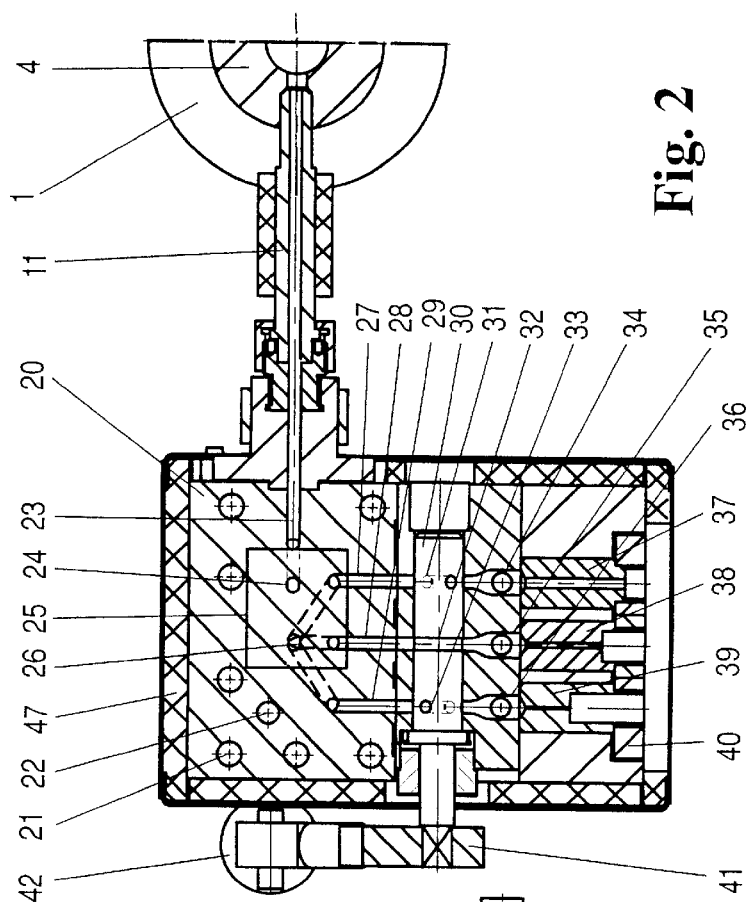
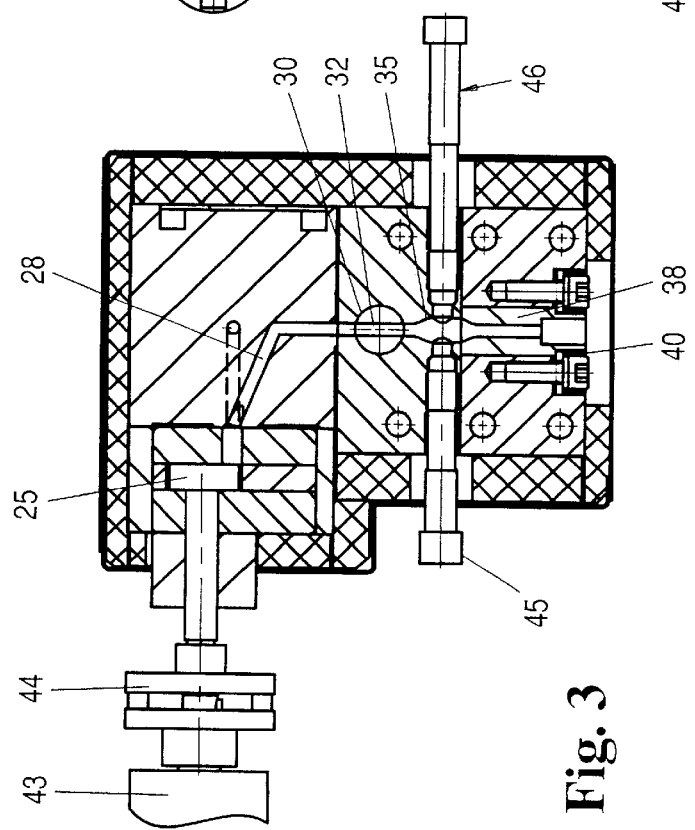

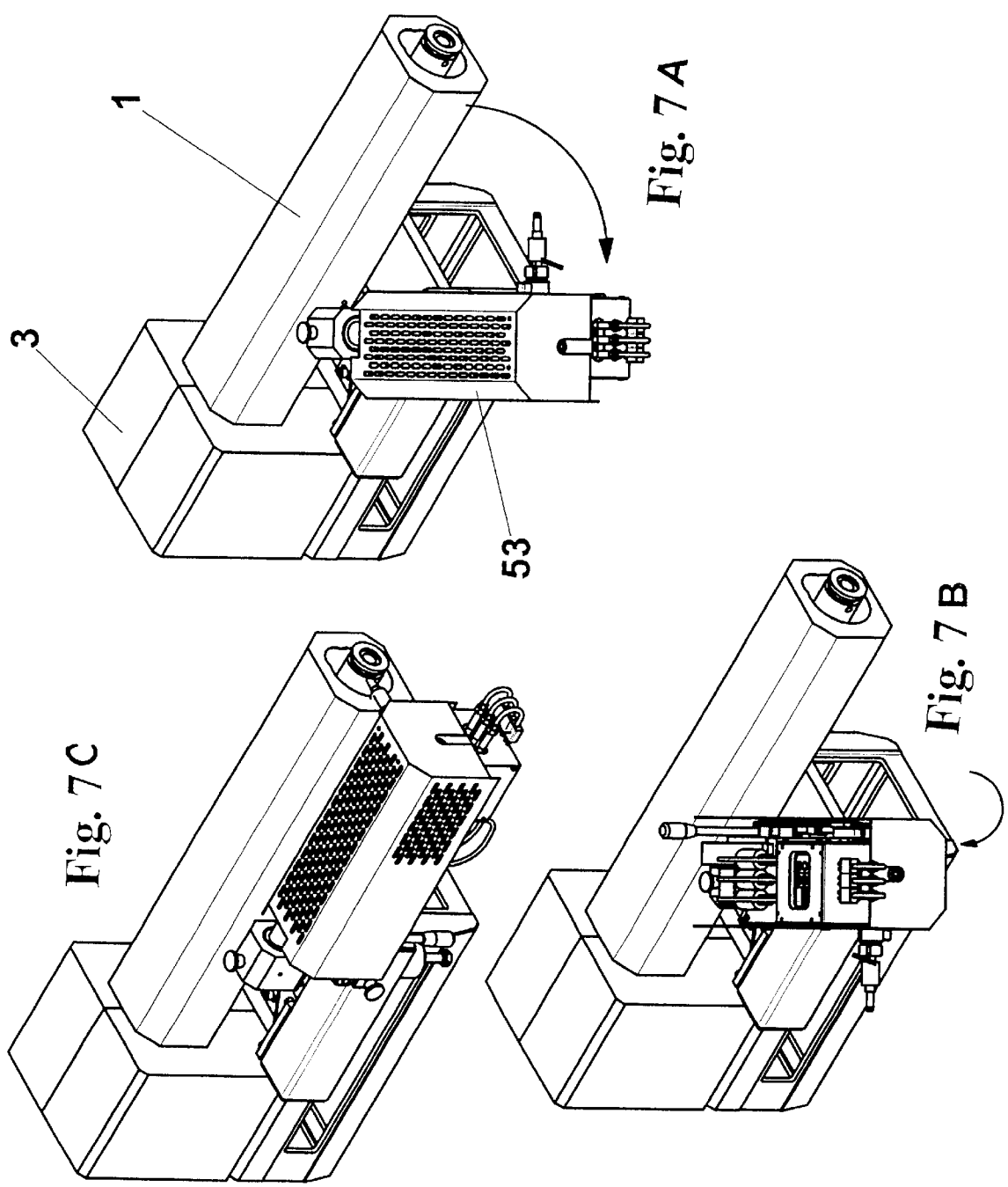

APPARATUS AND METHOD FOR MEASURING THE VISCOSITY OF PLASTIC MATERIALS

This is a continuation-in-part application of international patent application PCT/EP99/07477 filed Oct. 6, 1999 and claiming the priority of German application 198 46 579.3 filed Oct. 9, 1998.

BACKGROUND OF THE INVENTION

The invention relates to an apparatus for measuring the viscosity of plastic materials, particularly of polymer melts in accordance with the principle of determining the pressure drop of the material when flowing through a capillary and to a measuring method for determining the flow curve of such plastic material.

Such an apparatus and such a method are known for example from DE 42 20 157.

The quality control in the production of polymers comprises a number of examinations of different properties, such as the Theological properties, the determination of foreign particles in the melt, the determination of the chemical composition or, respectively, of the additives in a polymer.

In the past, the various properties were determined by separate measuring apparatus and methods. Today, however, the trend is to determine a multitude of properties in a single measuring apparatus or method.

Today, laboratory extrusion apparatus are in use in which at the same time or in successive steps:

a polymer is melted, rheological properties of the polymer, such as the viscosity, the melt flow index (MFI), or the melt volume index (MVI) are continuously determined.

a foil is produced which is continuously tested optically for the presence of foreign matter, such as gels, specks, black specks, or the foil is further utilized to continuously determine the content of certain additives by means of infrared spectroscopy.

The determination of the viscosity is therefore a partial task, which must be incorporated optimally into the total operating process of a laboratory extrusion apparatus.

With continuously operating so-called on-line rheometers, a distinction is to be made on one hand between so-called side stream rheometers which are fed by a side stream out of the extrusion apparatus and which discharge the material flow out of the capillary onto the ground and, on the other hand, the so-called in-line rheometers which are arranged in the mainstream of the melt between the worm kneader and the nozzle and wherein the melt, after passing through the rheometer, is returned to the main stream and discharged through the nozzle for further processing.

In the state of the art, the viscosity of a plastic material is determined, for example, by measuring the pressure loss upon flowing through a capillary of a predetermined dimension and length.

In that case, pre-conditions for the determination of the viscosity are:

the knowledge of the accurate amount of the material flowing through the capillary; for the examination of polymer melts, this amount is preferably defined by the use of a gear pump which is driven with a predetermined speed so as to provide a uniform flow volume of viscous material, the knowledge of the geometry of the measuring capillary; if a slot capillary is used, the width, the height, and the length of the capillary are known; if a round capillary is used, the diameter and the length are known, the adjustment of an accurate temperature of the melt and the area around the measuring capillary;

the knowledge of the specific weight of the substance to be measured;

the measurement of the pressure difference between inlet and outlet of a round capillary that is, respectively, the pressure difference between two points of a slot capillary. With this measurement value, a measuring point of the viscosity with a predetermined shear velocity can be obtained utilizing known mathematical equations. However, with polymer melts, the non-Newton or structure-viscous behavior is a big problem, that is, at different shear speeds, different viscosity values are obtained.

For determining the behavior of melts in the various, very different processes employed in the industrial plastic processing industry, very different shear speeds have to be covered, that is shear speeds in the range of about $1:10^4$.

With a capillary and a melt pump, normal ranges of 1:10 and maximal ranges of 1:100 of the shear speed can be covered. This, however, is possible only by varying the speed of the melt pump in a very wide range.

Therefore, for some time already, arrangements of multiple capillaries are used in order to increase the range of the shear speeds that can be measured.

In the known arrangement according to DE 42 20 157 A1, for example, slot capillaries with stepwise decreasing heights are utilized. In this way, the range of the shear speeds that can be measured is increased by the power of ten. In order to cover the wide range of shear speeds, additionally the speed of the melt pump must be changed substantially. When used as an in-line measuring apparatus, the travel time of the material in the relatively long nozzles is substantial whereby the material can be damaged.

DE 42 36 407 discloses an apparatus for measuring the viscosity of viscous materials particularly of polymer melts utilizing the principle of determining the pressure drop experienced by a mass flowing through a capillary with predetermined cross-section and predetermined length for use in a laboratory, particularly for the continuous measurement in a manufacturing plant especially with an integrated quality control. It includes a controllable melt pump for generating a predetermined melt flow and is installed in a heatable device and several capillaries are installed in the apparatus for accommodating a large range of flow speeds.

Ind. Lab. (1974) 40, pages 1467–1468 discloses a four channel viscosimeter, wherein melt can be supplied at the same time to four exchangeable capillaries. The mass flows in the capillaries act on a metal strip. The deformation of the metal strip is sensed and analyzed at the same time in all four capillaries.

In another known apparatus according to GB-A-2 271 856, several round capillaries are slideably so arranged that melt can be supplied to them from a melt pump in succession. It is a disadvantage in this arrangement that a uniform heating of the slideable capillaries is problematic. Especially, the use of a single mass pressure sensor for the complete pressure range to be measured is problematic, since, in this case, the measuring accuracy is insufficient in the very low pressure ranges with capillaries of large cross-section and very low shear velocities.

Furthermore, U.S. Pat. No. 4,677,844 discloses an apparatus for measuring the viscosity of viscous masses on the basis of the principle of determining the pressure drop of the mass when flowing through a capillary with a defined cross-section and defined length, wherein four capillaries are in communication with a cylinder and these capillaries are placed in communication with the surrounding atmosphere by operating a control mechanism. When a piston in the cylinder is operated, the mass contained in the cylinder is pressed through a selected capillary. That measurement step is repeated for each capillary.

In another arrangement, several capillaries are supplied with melt by several melt streams of a multiple gear pump. This is consequently a multiple arrangement of individual melt pumps each with an associated capillary.

Such an arrangement is disclosed for example in U.S. Pat. No. 4,425,790. Herein, three or four capillaries are arranged adjacent one another in series. From one capillary to the next, the size of the flow passages of the capillaries increases wherein the ratio of the capillary length to the capillary cross-section remains essentially the same for all capillaries. A heated polymer melt is pressed by means of a pressure pump through the capillaries with a constant volume flow rate. Sensors determine the pressure and temperature in each capillary. In this way, it is possible to determine the polymer viscosity in each capillary for different shear velocities.

In this way, large shear speed ranges can be measured with a single apparatus. However, the consumption of melt is doubled or tripled which results in increased new material expenses and causes re-granulation. In contrast, it is desirable, particularly in the continuous quality control, to minimize the amount of testing material being wasted.

In other known systems as they are disclosed, for example in DE 44 42 172 C2, FIG. 2, the melt is not discarded after passing through the capillary, but, is returned into the melt stream of the extruder. Although this method avoids, on one hand, the losses of material, the material is, on the other hand, subjected to greater time and thermal stresses when passing through the rheometer. In the subsequent optical examination, this may result in the indication of faults, which are not present in the original material, so that the measuring result of this subsequent examination is falsified. Also, U.S. Pat. No. 5,347,852 discloses such an in-line arrangement for the determination of the rheological properties of heated melts. Herein, with a first dosing pump, a melt stream is diverted from a mainstream to be processed. A second dosing pump pumps the diverted stream back into the main stream after it has been conducted through a capillary arrangement in which the pressure and temperature of the diverted melt stream have been determined. In the arrangement, the first and second dosing pumps are controllable independently from each other such that the pressure at the end of the capillary arrangement can be maintained essentially constant.

The arrangements known in the art consequently have many disadvantages, such as:
   either a small range of sheared velocities that can be covered;
   or a small measuring accuracy in certain ranges,
   or long dwell times with the chance of thermal damages;
   or high melt consumption resulting in increased expenses;
   or negative effects on the optical examination of melt being returned to the main stream.

It is the object of the invention to provide an apparatus and a measuring method by which the above listed disadvantages are avoided. This object is solved by an apparatus and a method according to the invention.

SUMMARY OF THE INVENTION

In an apparatus for measuring the viscosity of plastic materials including a heatable housing structure enclosing a controllable material pump for generating a certain material flow, and a plurality of capillaries, a melt distributor is provided in the supply line of the material from the material pump to the capillaries with which the material can be directed to either of the plurality of capillaries and each capillary is provided with a pressure and a material temperature sensor providing the values needed for determining the viscosity of the material.

The apparatus consists essentially of a multi-part rheometer body. The rheometer body is heated from all sides for maintaining an exactly defined melt temperature. The rheometer body includes an inlet passage to which the heated inlet pipe is flanged. The melt is usually prepared in a separate extruder in which it is plasticized and homogenized by being subjected to heat and shear energy. The main stream of the melt is discharged from the extruder by way of a suitable nozzle, for example in the form of a foil, which, after cooling, is utilized for determining the optical quality features of the polymer.

The melt is then supplied by way of a melt channel as a side stream to the gear pump, which is also integrated into the rheometer body. The material which is pre-pressurized by the extruder is supplied to the melt pump, which forces the melt with a constant volume flow through the discharge opening into the melt distributor (melt diverter).

Here, the melt stream is separated into several (2 to n) melt streams, which lead to a melt diverter. The melt diverter is preferably a cylindrical body, which is tightly fitted into the rheometer body. The cylinder includes a suitably arranged bore so that, upon rotation or axial displacement of the cylinder by a predetermined amount, the bore is aligned with another channel for supplying melt to another capillary. This melt diverter is so controlled that a melt stream is conducted only to one of the capillaries, which are firmly installed in the rheometer body downstream of the melt diverter. In front of each capillary, an increased volume pressure-measuring chamber is provided which facilitates the installation of a membrane-type pressure sensor for each of the measuring capillaries.

After flowing through the capillary, the melt exits depressurized and is collected and cooled in a container disposed below.

The individual measuring capillaries are mounted in the rheometer by means of clamping bolts so that they are easily exchangeable.

The measuring procedure is as follows:

The capillaries are so selected that, on one hand, a large shear speed range can be covered (about 1:1000) and, on the other hand, the pressure build-up will not exceed the values admissible for the operation of the melt pump and the pressure sensors. For each measuring range, an optimally suitable pressure sensor is installed.

The pump is set to operate at a certain speed for providing a certain flow volume. The melt diverter is positioned for directing the flow to the first capillary. After a predetermined flushing period, several measurements are performed for determining a reliable average value.

After a certain time, the melt diverter is readjusted so as to direct the melt flow to the next capillary. This process may then be repeated for a third capillary. The measurement at constant throughput of the melt pump provides in this case already three points of a flow curve in the shear velocity range of up to 1:1000 or more. This measuring result is sufficient for most applications in the continuous quality control.

After completion of a measuring series, a computation procedure for the determination of the three measuring points of a flow curve is automatically initiated. Herefrom, for example, the Careau equation, the complete flow curve is calculated and a standard value for the flowability, for example, an MFI-value is determined. In this way, a continuously corrected viscosity value is available in the process control in the form of a curve or as an individual value.

If in the laboratory or in research and development, a larger measuring range or a more accurate determination of the flowability curve is desired, additionally the speed of the melt pump may be changed whereby a range of the shear velocity of more than $10^4$ can be covered.

The advantages of the apparatus according to the invention are therefore as follows:

- a wide range of the shear speed of up to 1:1000 is covered already with a constant pump speed and a constant melt stream without affecting the main melt stream of the extruder,
- the flow curve can properly be established by the determination of the three different measuring points for the whole shear speed range without the need for changing capillaries by hand and calibrating them;
- with a variable pump speed a shear speed range of up to $1:10^4$ can be covered; with the additional control of the pump speed, for example with a second pump speed, six or even eight points of a flow curve can be determined;
- the measurement values are highly accurate and reproducible as an optimal pressure sensor is provided for each capillary;
- the consumption of polymer material is relatively low since, by using of a melt diverter, the melt material flow can be directed to one capillary after the other; and
- the flow curve and a standard fixed value (for example MFI) are determined fully automatically.

The advantages and features of the present invention will become apparent from the following description of embodiments in connection with the drawings.

BRIEF DESCRIPTION OF THE DRAWINGS

FIG. 2 is a cross-sectional view of the apparatus according to the invention;

FIG. 3 shows a longitudinal cross-section of a melt diverter with three bores;

FIG. 7A, FIG. 7B, and FIG. 7C show an apparatus according to the invention in operating position (normal operating position) and in two cleaning positions.

DESCRIPTION OF A PREFERRED EMBODIMENT

Figure 1:
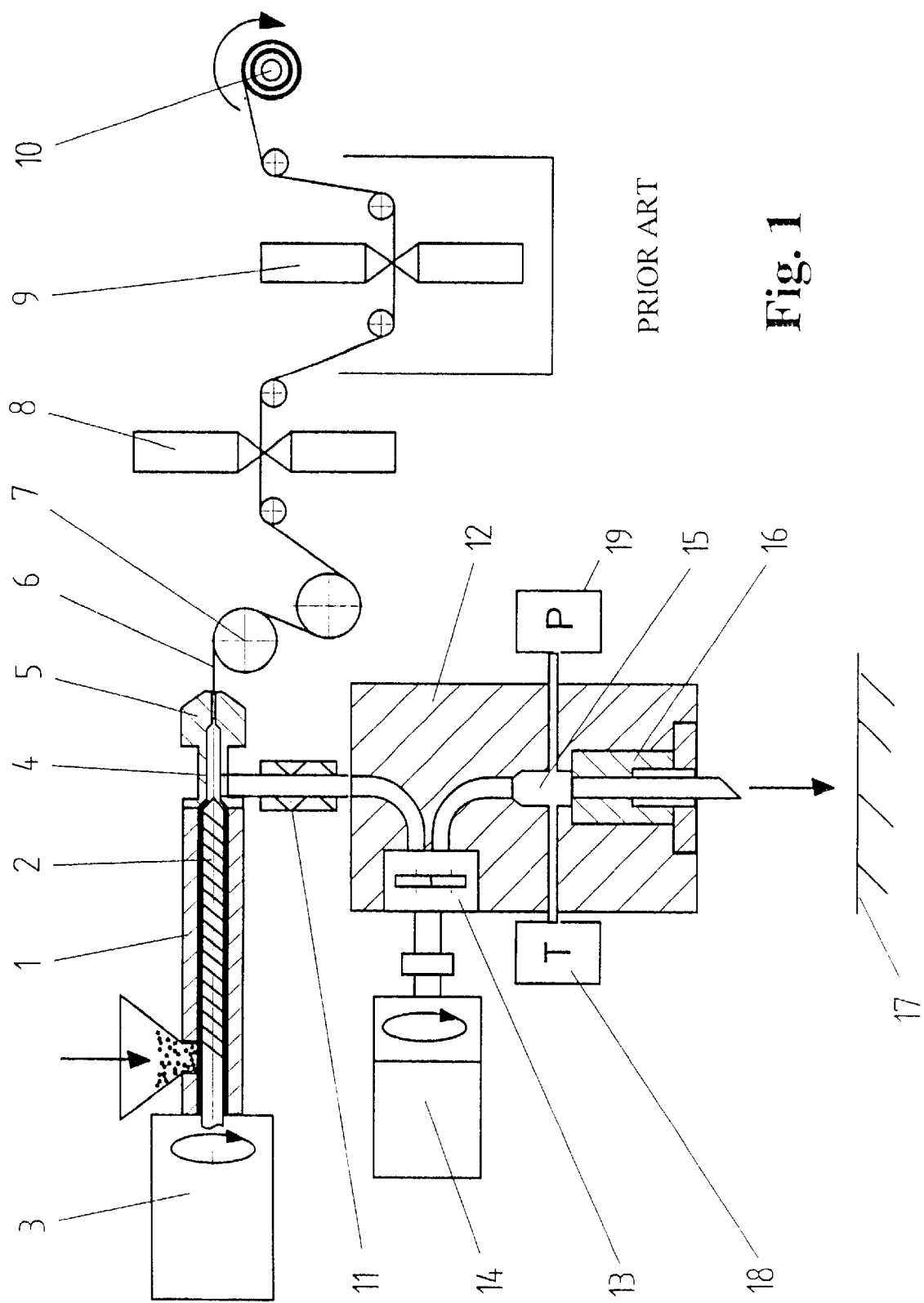
FIG. 1 is a representation, in principle, of a laboratory extrusion apparatus with a side stream rheometer.

FIG. 1 shows, in principle, an example of a laboratory extrusion apparatus, which is used in the quality control of polymers. In the heated cylinder 1 of the extruder, the polymer is melted and, by the rotation of the worm 2, which is provided for by the drive 3, is supplied to the adapter 4. From there, the melt reaches the nozzle 5 through which it is extruded for example as a flat foil 6. (In a similar way, instead of a flat foil nozzle, a bubble foil nozzle may be used for producing a bubble foil). The cooling rollers 7 of the foil pulling device cool the foil and direct the foil to an examination arrangement 8 (for example, for an optical examination for enclosures) and a testing arrangement 9 (for example, for examining the chemical composition). Then the foil is wound onto a spool 10.

From the adapter 4, a side stream of the melt is diverted by way of the melt pipe 11 to the heated rheometer body 12 and there again directed to the melt pump 13. The melt pump 13 is driven by the drive 14, which is controllable. By way of the melt bore 15, the melt is forced through the capillary 16 from which it is discharged to the ground 17. In the process, the melt temperature and the melt pressure ahead of the capillary are measured by means of sensors 18 and, respectively, 19.

FIG. 2 is a cross-sectional view of the melt supply arrangement and the rheometer body of the apparatus according to the invention for an exemplary apparatus with three capillaries. From the cylinder 1 or, respectively, the adapter 4, the melt is supplied through the heatable melt tube 11 to the rheometer body 20.

The rheometer body 20 is heated by heating elements 21. The temperature is measured by the temperature sensors 22 for an accurate control of the temperature. The heat insulation 47 guarantees a uniform temperature distribution. The melt is conducted, by way of the melt passage 23, through the body 20 up to the inlet opening 24 of the melt pump 25, which is flanged to the back side of the rheometer body. Through the discharge opening 26, the melt leaves the pump 25 and, in the given example, is divided into three individual flows corresponding to the passages 27, 28, and 29.

From one of these passages, the melt flows through one of the transverse bores 31, 32, or 33 of the melt diverter 30 to one of the pressure chambers 34, 35, or 36. The position of the melt diverter 30 by which one of the transverse bores is open is set by the pneumatic or hydraulic cylinder 42 by way of the ratchet structure 41.

From the pressure chambers, the melt flows through the capillaries 37, 38 and 39, one at a time, to the outside where it is no longer under pressure. After removing the retaining member 40, the capillaries can be removed.

FIG. 3 shows the apparatus according to the invention in a longitudinal cross-section. The drive motor 43 drives the melt pump 25 by way of an articulated joint coupling 44. The melt stream from the pump is conducted to the melt diverter 30 by way of the passage 28. The melt then flows through the transverse bore 32 into the pressure chamber 35. In this area, a sensor 45 measures the melt pressure and a sensor 46 measures the melt temperature. Through the capillary 38, the melt flows to the outside without any back-pressure.

The well-defined value for the melt volume flow, which is obtained by the use of the melt pump 25, and the values for the melt pressure and the melt temperature as determined by the sensors 45 and 46 can be supplied, by way of a converter (not shown), to a computer (not shown) where the desired flow curves can be calculated.

In the embodiments as shown in FIGS. 2 and 3, the melt distributor is in the form of an axially symmetrical melt diverter, which includes n (wherein n=2, 3, 4, . . . ) transverse passages for conducting the melt. The melt distributor can be switched, by rotational movement, from a position associated with one of the n capillaries to a position associated with an adjacent capillary.

Figure 4:
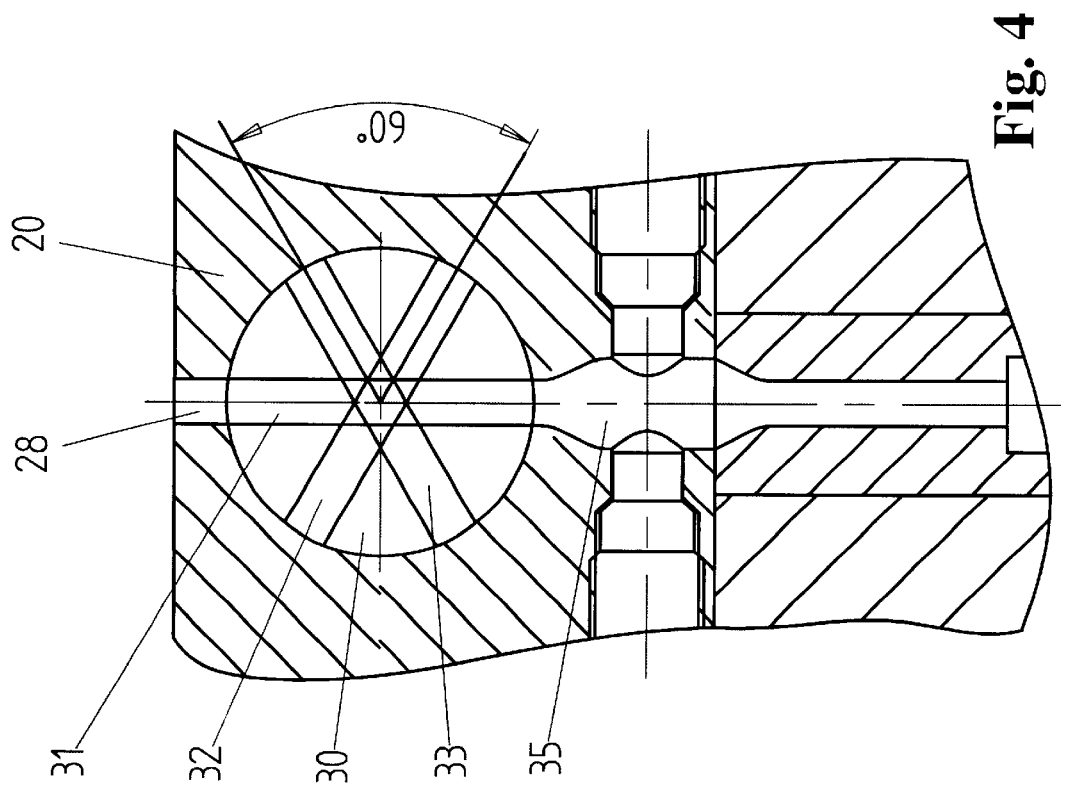
FIG. 4 shows a longitudinal cross-section of a melt diverter with three bores.

Preferably, the melt distributor includes three radially arranged transverse bores for conducting the melt. FIG. 4 shows a section of FIG. 3. The bores 31, 32, and 33 in the melt distributor 30 are displaced each circumferentially by 60° so that, with a rotational movement of 60°, the melt can be supplied to the next one of all together three capillaries. Consequently, the flow path from the supply passage 28 to the pressure chamber 35 in front of the capillary 38 as again open after three rotation steps.

Figure 5:
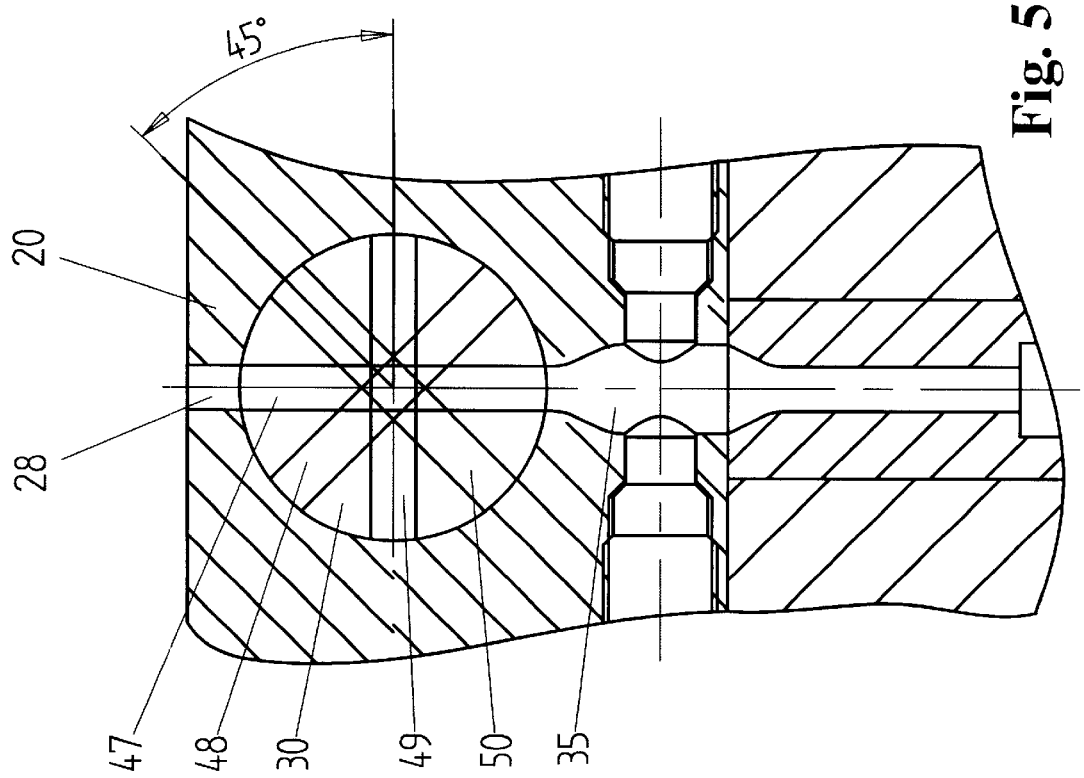
FIG. 5 shows a longitudinal cross-section of a melt diverter with four bores.

In another embodiment according to FIG. 5, the melt distributor is provided preferably with four transverse bores 47, 48, 49, and 50 for controlling the melt flow and the bores are displaced circumferentially so that, with a rotational movement of the melt distributor by 45°, the melt can be supplied to the respective next one of the four capillaries.

The drive for the rotation of the melt distributor can be operated by a servomotor with a stepping control such that the rotational movement occurs always in the same direction.

In still another embodiment (FIG. 6) two capillaries are provided and the rotational movement of the melt distributor is effected by means of a hydraulic or pneumatic cylinder or by an electrical or magnetic drive (not shown). In this arrangement, the melt distributor is rotated back and forth between one and the other position.

Figure 6:
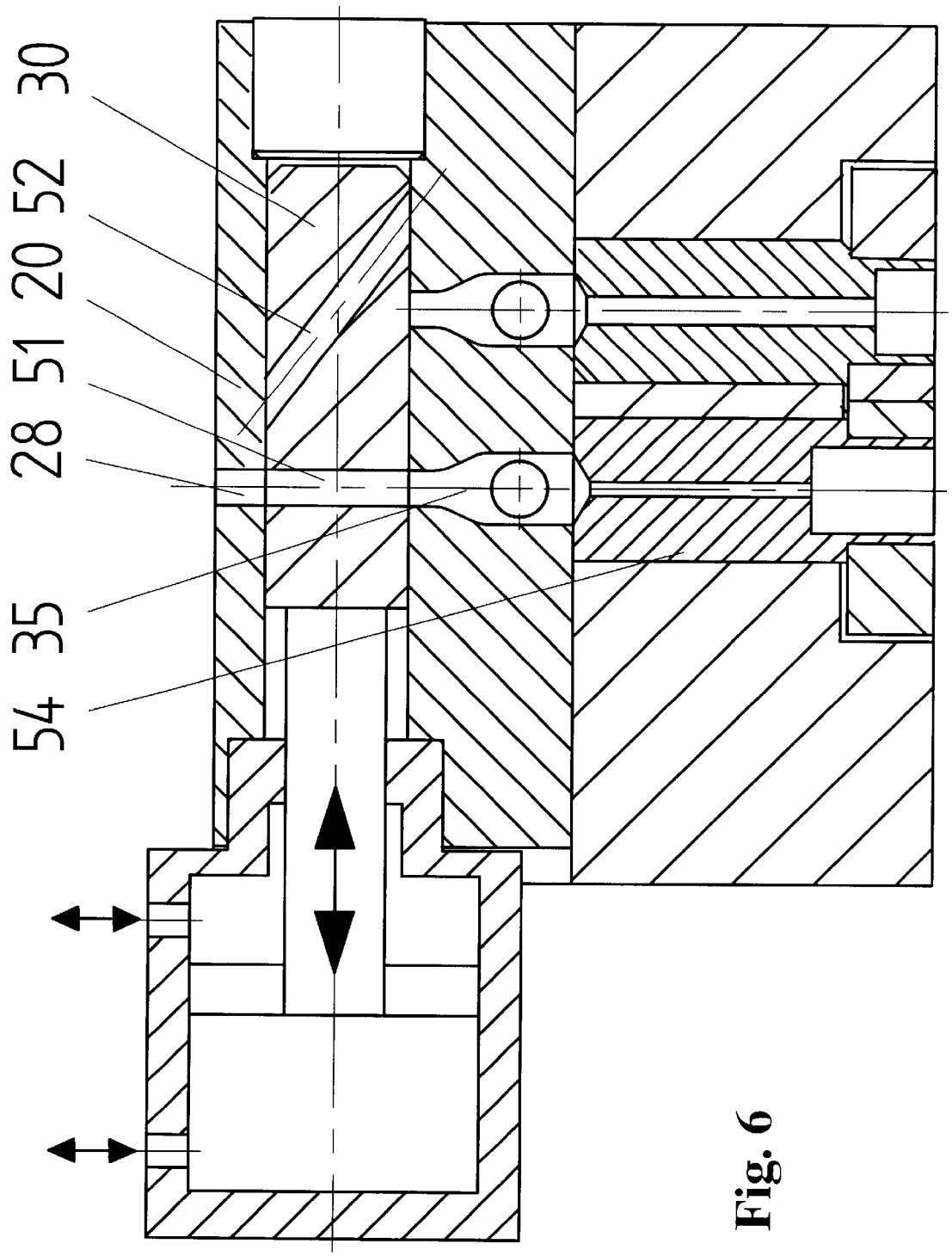
FIG. 6 is a cross-sectional view of an apparatus according to the invention with an axially slideable melt diverter.

Alternatively, the melt distributor may be in the form of a slide, and the melt flow paths to the various capillaries can be opened successively by sliding the slide in an axial direction. The slide movement can be initiated electro-mechanically, pneumatically, or hydraulically. FIG. 6 shows an example of such an arrangement wherein the melt distributor is in the form of a slide which is moved axially by actuation of a cylinder so that the melt can flow selectively through the bores 51 or 52 to the downstream pressure chamber 35 and from there to the capillary 54.

As shown in FIG. 7 in a perspective view of the extruder with the cylinder 1 and the drive 3, the whole rheometer 53 can be pivoted to one side (Pos. A) and additionally upwardly about an axis which extends parallel to the cylinder axis of the extruder when in a normal operating position.

Preferably, the whole rheometer arrangement with the rheometer body 20, the melt pump 25, and the drive 43 is mounted to the extruder substructure and is pivotable away from the extruder cylinder to one side by 15° to 90°; and upwardly about an axis which extends parallel to the cylinder axis of the extruder by 90° to 180° so that, after removal of an adapter from the extruder, cleaning is facilitated.

It is furthermore advantageous if the whole rheometer arrangement is disposed on a movable stand (not shown) so that, after disconnecting the adapter, the rheometer can be wheeled away from the extruder.

What is claimed is:

1. An apparatus for measuring the viscosity of plastic materials based on the principle of determining the pressure drop of the material when flowing through a capillary having a certain cross-section and a certain length, said apparatus comprising a heatable housing structure,
  a controllable material pump for generating a certain material flow installed in said heatable housing structure, a plurality of capillaries mounted in said housing structure for covering a relatively large range of flow speeds of said material,
  said capillaries having different dimensions and each capillary having associated therewith a pressure sensor adapted to a respective pressure range, and
  a movable melt distributor in the form of a cylindrical body for directing the melt flow from the melt pump to one capillary at a time,
  said cylindrical body including transverse bores arranged in such a way that, by changing the position of the melt distributor, melt can be conducted through another one of the plurality of capillaries and each capillary having a material temperature sensor associated therewith.

2. An apparatus according to claim 1, wherein said melt distributor is adjustable by one of a hydraulic and a pneumatic cylinder and a ratchet device.

3. An apparatus according to claim 1, wherein said melt distributor is in the form of a slide for controlling the melt paths by movement of the slide in axial direction to direct the melt flow to the various capillaries, said slide movement being initiated by one of electro-mechanical, pneumatic, and hydraulic means.

4. An apparatus according to claim 1, wherein said melt distributor is in the form of a rotationally symmetrical melt diverter which includes several transverse bores for controlling the melt flow, said melt diverter being movable by rotation from a position providing for melt flow to one of the plurality of capillaries to a position providing said melt flow to the next capillary.

5. An apparatus according to claim 4, wherein said melt distributor includes three transverse bores arranged radially for conducting the melt and said bores are displaced circumferentially by 60° so that, by rotation of the melt distributor around its axis of rotation by 60°, melt can be supplied to the following of the three capillaries.

6. An apparatus according to claim 4, wherein said melt distributor is provided with four transversely arranged melt conducting bores, and the bores are displaced circumferentially by 45° so that, by rotation of the melt distributor about its axis of rotation by 45°, melt can be supplied to the next one of the four capillaries.

7. An apparatus according to claim 4, wherein a servo motor with a stepping structure is provided for rotating said melt distributor so that rotation of the melt distributor occurs always in the same direction.

8. An apparatus according to claim 4, wherein only two capillaries are provided and the movement of said melt distributor occurs by one of a hydraulic cylinder, and a pneumatic cylinder in such a way that said melt distributor is moved back and forth from one position to the other.

9. An apparatus according to claim 1, wherein said apparatus includes an extruder, a rheometer body, a melt pump and a drive mounted on a substructure so as to be pivotable away from the extruder by 15 to 90° and upwardly about an axis extending in the normal operating position parallel to the axis of the extruder whereby, after disconnection of the adapter from the extruder, cleaning is facilitated.

10. A method for measuring the viscosity of plastic materials, based on the principle of determining the pressure drop of the material when flowing through a capillary having a certain cross-section and a certain length, said method comprising the steps of:
  providing a predetermined material volume flow in an environment having a predetermined temperature,
  providing several stationary capillaries of different dimensions for covering a relatively large range of flow speeds,
  determining for each capillary measurement values for the pressure of the material,
  directing a predetermined melt volume flow to one of the capillaries utilizing a movable melt flow distributor in the form of a cylindrical body provided with transverse bores,
  changing the position of the material distributor so that the material is supplied to a respective one of the several capillaries,
  and calculating from the average measurement values obtained for pressure and temperature for each of the capillaries, and with the predetermined material flow volume, the flow curves characteristic for the material.

* * * * *